Jan. 23, 1940. C. A. BROWN, 2D Plant Pat. 355
GERANIUM
Filed Oct. 31, 1938
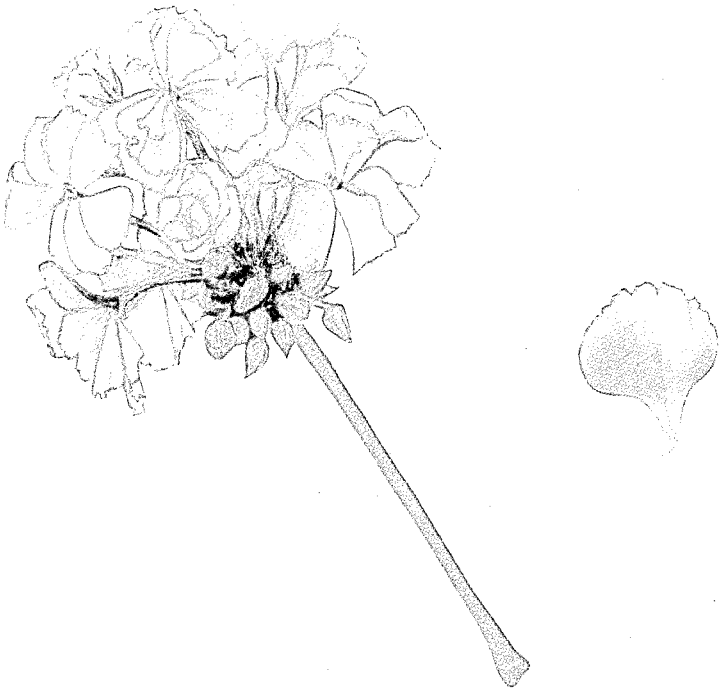
Inventor:
Charles A. Brown II
By Brown, Jackson, Boettcher & Dienner
Attys Patented Jan. 23, 1940

Plant Pat. 355

UNITED STATES PATENT OFFICE

355

GERANIUM

Charles A. Brown, II, Hinsdale, Ill., assignor to Hinsdale Cemetery Company, Hinsdale, Ill., a corporation of Illinois Application October 31, 1938, Serial No. 238,103

1 Claim. (Cl. 47—60)

The present invention relates to a new and distinct variety of geranium characterized primarily by a serrated or toothed edge of each petal.

This type of geranium, being sturdy and a profuse bloomer, yet with a tendency to the dwarf, makes an ideal pot geranium. My new variety is also valuable for borders and window boxes.

The novelty of the geranium resides particularly in the characteristics above set forth. However, other novel features will become apparent as the description progresses.

My new variety of geranium originated as a sport from the pink Fiat geranium, as a parent. I saw the original sport attached to the parent Fiat, and have preserved the original plant, which still bears the sport. This new variety of geranium has been reproduced by cuttings.

My new variety resembles the parent Fiat in its habits of growth, its foliage, and the shape of its buds and flowers. The foliage is relatively dark green in color and the leaves have a very light green marginal zone and a dark green intermediate zone.

The particular habits of growth of my new variety which resemble those of the parent Fiat are the characteristics of strong, bushy, vigorous growth and the tendency toward dwarfness.

Another distinctive feature of my new variety is its blooming habit. The geranium blooms continually throughout the spring and summer, and will do well wherever geraniums may be grown.

My new variety produces from three to eight clusters of flowers and buds at one time, as does the parent geranium. The well-rounded flower clusters are borne on a stiff strong stem or peduncle. The cluster is an umbel and is relatively large in size, measuring from three to five inches across.

The individual flower measures from one and one-half to two inches across, according to season. Each flower has approximately eight petals. The border of each petal is irregularly or unequally crenate, substantially as shown in the right hand detail view of the drawing. The veining toward the receptacle end of the petal is considerably more pronounced in my new variety than in the parent.

My new variety of geranium has been found to hold its distinguishing characteristics through succeeding generations by means of asexual reproduction, propagation of several hundred plants being made from cuttings.

The original illustrations show in full color and approximately natural size, a flower cluster with buds, partly-opened buds and flowers in full bloom. The right hand drawing shows a single petal enlarged for clarity of illustration.

The following detailed description was made from a geranium grown in the greenhouse of The Hinsdale Cemetery Company at Hinsdale, Illinois.

Description

*Flower*

Blooming habit:
- Location where observations were made—The Hinsdale Cemetery Company greenhouse.

Recurrent:
- Continually during spring and summer in this climate.

Bud:
- *Size.*—Normal.
- *Form.*—Ovoid.
- *Color.*—Medium green.
- *Sepals.*—Fuzzy, open straight when bud begins to open.
- *Calyx.*—Medium green, five sepals.
- *Peduncle.*—Fairly short, fuzzy, medium green.
- *Pedicels.*—½″ to 1″ in length, fuzzy, erect, sturdy.
- *Opening.*—Opens well, little affected by adverse conditions.
- *Size.*—Normal.
- *Borne.*—Clusters.
- *Petalage.*—Approximately eight petals.
- *Color.*—According to an approximation based on the Munsell "Book of Color", the hue is red, the value is above 6 (probably between 6, 7, and 8), and the chroma or saturation is brighter than Munsell registers at high values.
- *Variations.*—None.
- *Discoloration.*—Retains true color even in hot weather.

Petals:
- *Texture.*—Thick, little affected by weather.
- *Form.*—Rather broad spatulate, margins irregularly or unequally crenate.
- *Fragrance.*—Slight.
- *Lasting quality.*—On plant very long.

Genital organs:
- *Stamens, anthers.*—Small, average.
- *Color.*—Light brown.
- *Stamens, filaments.*—Medium.
- *Color.*—White.
- *Pistil, styles.*—One, light green, fuzzy.

*Pistil, stigmas.*—Pink, equal in number to stamens.

Plant:

*Form.*—Bush.

*Growth.*—Vigorous with tendency to dwarfness.

Foliage:

*Size.*—Large.

*Quantity.*—Normal.

*Color.*—Upper surface dark green with darker green intermediate zone and very light marginal zone.

*Shape.*—Cucullate or disk-shaped.

*Texture.*—Soft-fuzziness on upper and under surface of leaves.

*Margin.*—Serrately lobed.

*Disease.*—Resistant.

*Stem.*—Medium size, neither slender nor thick. Fuzzy, firm and capable of supporting heavy cluster.

The geranium shown and described is claimed by me to be distinguished by the following most important feature: The formation of the blossoms, particularly the irregularly crenate petals of the flower.

The foregoing feature is believed and claimed by me to be new in such type of geranium.

I claim:

A new and distinct variety of geranium characterized by a flower having irregularly or unequally crenate petals.

CHARLES A. BROWN, II.